United States Patent [19]
Yamaguchi et al.

[11] Patent Number: 5,484,948
[45] Date of Patent: Jan. 16, 1996

[54] BISMALEIMIDE COMPOUNDS

[75] Inventors: Keizaburo Yamaguchi, Chiba; Tatsuhiro Urakami; Yoshimitsu Tanabe, both of Yokohama; Midori Yamazaki, Hiratsuka; Shoji Tamai; Norimasa Yamaya, both of Yokohama; Masahiro Ohta, Ohmuta; Akihiro Yamaguchi, Kamakura, all of Japan

[73] Assignee: Mitsui Toatsu Chemicals, Inc., Tokyo, Japan

[21] Appl. No.: 284,103

[22] Filed: Aug. 2, 1994

Related U.S. Application Data

[62] Division of Ser. No. 5,276, Jan. 19, 1993, Pat. No. 5,364,967, which is a division of Ser. No. 601,424, Oct. 23, 1990, Pat. No. 5,206,438.

[30] Foreign Application Priority Data

| Oct. 24, 1989 | [JP] | Japan | 1-275050 |
| Mar. 6, 1990 | [JP] | Japan | 2-052779 |
| May 11, 1990 | [JP] | Japan | 2-119679 |
| May 24, 1990 | [JP] | Japan | 2-132711 |
| Jul. 6, 1990 | [JP] | Japan | 2-177518 |
| Jul. 19, 1990 | [JP] | Japan | 2-177517 |
| Aug. 10, 1990 | [JP] | Japan | 2-210246 |

[51] Int. Cl.$^6$ .............................................. C07D 207/444
[52] U.S. Cl. ................................. 548/549; 548/548
[58] Field of Search ................................. 548/546, 548, 548/549

[56] References Cited

U.S. PATENT DOCUMENTS

| 5,070,163 | 12/1991 | Stockinger et al. | 526/259 |
| 5,206,438 | 4/1993 | Yamaguchi et al. | 564/315 |

FOREIGN PATENT DOCUMENTS

| 253891 | 1/1988 | European Pat. Off. |
| 317216 | 5/1989 | European Pat. Off. |
| 23250 | 7/1971 | Japan . |
| 8644 | 5/1972 | Japan . |
| 11500 | 6/1972 | Japan . |
| 264566 | 11/1988 | Japan . |
| 1246247 | 2/1989 | Japan . |
| 500866 | 3/1988 | WIPO . |

OTHER PUBLICATIONS

S. Smolinski and E. Halasa, "Aromatic Nitro-Ethers and Aromatic Amino-Ethers of 3,5,3',5'-Substituted 2,2-Bis(4Hydroxyphenyl)Propane and its Analogues"; 1974, pp. 1459–1467.

Stockinger et al, Chemical Abstracts, vol. 114, (1990) 67942q.

Primary Examiner—Richard L. Raymond
Assistant Examiner—B. Bembenick
Attorney, Agent, or Firm—Burns, Doane, Swecker & Mathis

[57] ABSTRACT

Disclosed is an aromatic diamine compound represented by the formula (I)

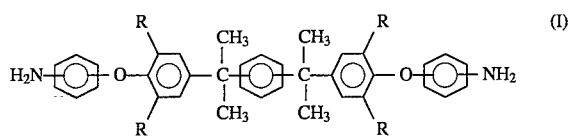

wherein R is H or $CH_3$.

Also disclosed is a bismaleimide compound represented by the formula (IV)

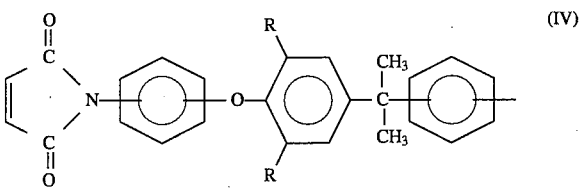

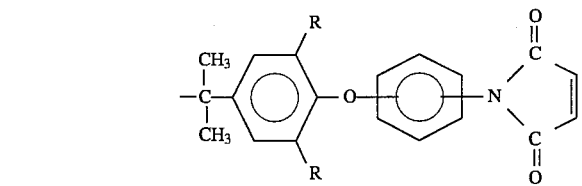

wherein R is H or $CH_3$,

A resin forming composition comprising these compounds is also disclosed. The compounds are useful as raw materials for resins, and the resin forming composition and the resin can provide excellent heat resistance and impact resistance and low hygroscopicity.

4 Claims, 4 Drawing Sheets

BISMALEIMIDE COMPOUNDS

This application is a divisional of application Ser. No. 08/005,276, filed Jan. 19, 1993 (Now U.S. Pat. No. 5,364, 967), which is a divisional of application Ser. No. 07/601, 424, filed Oct. 23, 1990, which is now U.S. Pat. No. 5,206,438.

BACKGROUND OF THE INVENTION

The present invention relates to aromatic diamine compounds which can be used as raw materials for polyimide, polyamide, bismaleimide or epoxy resins. The compounds can also be employed as curing agents. The invention also relates to a method for preparing the compounds.

Furthermore, the present invention relates to bismaleimide compounds which are useful as raw materials for heat-resistant resins, and which can be obtained from the aforementioned aromatic diamine compounds. The invention also relates to a method for preparing the compounds.

In addition, the present invention relates to thermosetting resin forming compositions, and ultimately the resins, which are obtained from the aforementioned aromatic diamine compounds and bismaleimide compounds, as well as a method for preparing the composition.

In recent years, raw materials for heat-resistant resins have been required to provide a combination of good thermal and mechanical properties, as well as certain other characteristics which composites should exhibit such as flexibility and moldability/workability.

In this regard, polyimide resins have been used. While providing some excellent properties, they typically exhibit poor moldability/workability.

An example of such a polyimide is an aromatic polyimide made by Du Pont and marketed under the tradename "Vespel". This polyimide can be prepared from 4,4'-diaminodiphenyl ether and pyromellitic anhydride. It is insoluble and unmeltable. Thus, when it is molded, a special procedure such as powder sinter molding must be used. Unfortunately, this molding technique cannot be easily used for the preparation of articles having complex shapes. During manufacturing of complex shaped articles, additional operations such as cutting are necessary. As a result the polyimide is difficult to mold and costs increase.

To address those drawbacks associated with polyimide resins, a variety of strategies have been formulated, primarily focusing on improving the diamine component of the raw materials. For example, there have been attempts to introduce an ether linkage group or an isopropylidene group into the molecule and to increase the molecular chain. Unfortunately, these techniques have not effectively provided the flexibility and moldability/workability characteristics necessary for composite materials.

A typical example of a bismaleimide is N,N'-(methylene-di-p-phenylene)bismaleimide disclosed in Japanese Patent Laid-open Nos. 47-8644 and 47-11500. However, this bismaleimide compound is substantially insoluble in common organic solvents such as ketone and petroleum solvents. And, when a polyimide resin is prepared using this compound, the occupation ratio of the polyimido group in the polymer structure is high. Therefore, the polymer is hard, brittle and provides extremely poor flexibility and high hygroscopicity. The effective application of the bismaleimide compounds is accordingly limited considerably.

Recently, in an effort to eliminate such disadvantages, much attention has been given to the development of long-chain bismaleimide compounds. For example, Japanese Patent Laid-open No. 63-500866 discloses a bismaleimide compound having three benzene rings and having the following structure represented by formula (X):

In addition, Japanese Patent Laid-open No. 63-264566 discloses a bismaleimide compound having four benzene rings and having the following structure represented by the formula (XI):

However, even with these bismaleimide compounds and polymers prepared from the compounds, an effective balanced combination of heat resistance, flexibility, adhesion to a metal and inorganic materials, and workability is not provided.

Thermosetting resins having an imido structure have been effectively used to prepare molded articles having excellent electrical insulating properties, heat resistance and dimensional stability. Therefore, this type of resin has been utilized in many industrial fields.

However, thermosetting resins obtained by subjecting aromatic bismaleimides alone to heat polymerization are very brittle and provide poor flexibility, although they do provide excellent heat resistance. To address this drawback, attempts have been made to develop thermosetting resin forming compositions comprising an aromatic bismaleimide and an aromatic diamine. For example, a polyaminobismaleimide resin made by Rhone Poulenc, and marketed under the tradename "Kelimide" comprising N,N'-4,4'-diphenylmethane-bismaleimide and 4,4'-diaminodiphenylmethane has been widely utilized for impregnating varnishes, laminates and molded articles (See Japanese Patent Publication No. 46-23250). However, this type of thermosetting resin is still unsatisfactory in terms of impact resistance and flexibility. Furthermore, when these thermosetting resins are used as base materials for electrical and electronic parts, they exhibit poor moldability/workability and high hygroscopicity, which adversely affect electrical properties.

SUMMARY OF THE INVENTION

Therefore, an object of the present invention is to provide a diamine compound which is useful as a raw material for various resins and which can provide excellent flexibility and moldability/workability. It is likewise an object to provide a method for preparing such a diamine compound.

Another object of the present invention is to provide a bismaleimide compound which is readily soluble in common solvents and can be used to prepare a polymer having improved properties. It is likewise an object to provide a method for preparing such a bismaleimide compound.

Still another object of the present invention is to provide a thermosetting resin forming composition, as well as a resin, which can provide excellent mechanical strength, particularly in terms of impact resistance, and which has low hygroscopicity. It is also an object to provide a method for preparing such a composition and resin.

Accordingly, the present invention is directed to a novel aromatic diamine compound represented by formula (I):

wherein R is H or CH3.

The diamine compound of the invention can be obtained by reacting a compound represented by the formula (II):

with a nitrobenzene compound such as nitrochlorobenzene or dinitrobenzene in the presence of a base in an aprotic polar solvent to obtain a compound having the formula (III):

The compound of formula (III) is then reduced to obtain the diamine compound of the invention.

The present invention provides a relatively easy technique for providing the novel diamine, the diamine being useful as a raw material for resins and which provides excellent flexibility and moldability/workability, or as a curing agent.

Furthermore, the present invention provides a novel bismaleimide compound which comprises a skeleton having five benzene rings and is represented by the formula (IV):

wherein R is H or $CH_3$.

The bismaleimide compound represented by the formula (IV) is advantageously soluble in common solvents such as toluene or xylene. A polyimide prepared using this type of bismaleimide has excellent heat resistance and flexibility, as well as low hygroscopicity.

The bismaleimide of the present invention can be prepared by a dehydration/condensation reaction between a diamine component and maleic anhydride. This dehydration/condensation reaction can be carried out by dissolving or dispersing the diamine of the invention, maleic anhydride and an acid catalyst in a predetermined solvent, and then heating the resulting solution or dispersion under reflux. More specifically, a diamine compound of formula (I) can be reacted with maleic anhydride in the presence of an acid catalyst under heating/reflux of an organic solvent, while any water which is produced is removed from the system.

The bismaleimide compound of the present invention can be used as a raw material to prepare the novel addition-type polyimide of the invention. Since the occupation ratio of the imido group in the molecule of the bismaleimide compound is low, the polyimide resin made from this compound can provide improved flexibility and low hygroscopicity. Therefore, when using the bismaleimide compound of the present invention, blending properties and performance of the thermosetting-type polyimide resin can be considerably improved.

Moreover, by the present invention there is also provided a thermosetting resin forming composition comprising the diamine compound of formula (I) and the bismaleimide compound of formula (IV). The thermosetting resin forming composition of the present invention gives a thermosetting resin which has excellent heat resistance, impact resistance and toughness, as well as low hygroscopicity. Thus, it can be expected that the composition will be effectively applied to electrical and electronic parts, various structural parts, sliding parts and many other uses. The composition of the present case is industrially useful and effective.

DETAILED DESCRIPTION OF THE PREFERRED EMBODIMENTS OF THE INVENTION

According to the present invention, preferable diamine compounds are those compounds of formula (I) wherein the amino groups of the aminophenoxy groups are bonded to the meta- or the para positions thereof, and those compounds of formula (I) wherein the two aminophenoxy-(methyl or dimethyl)-α,α-dimethylbenzyl groups are bonded to the meta- or the para positions of the central benzene ring.

Examples of preferable diamine compounds include; (i) 1,4-bis[4-(4-aminophenoxy)-α,α-dimethylbenzyl]benzene, (ii) 1,3-bis[4-(4-aminophenoxy)-α,α-dimethylbenzyl]benzene, (iii) 1,4-bis[4-(3-aminophenoxy)-α,α-dimethylbenzyl]benzene, (iv) 1,3-bis[4-(3-aminophenoxy)-α,α-dimethylbenzyl]benzene, (v) 1,4-bis[4-(4-aminophenoxy)-3,5-dimethyl-α,α-dimethylbenzyl]benzene, (vi) 1,3-bis[4-(4-aminophenoxy)-3,5-dimethyl-α,α-dimethylbenzyl] benzene, (vii) 1,4-bis[4-(3-aminophenoxy)-3,5-dimethyl-α, α-dimethylbenzyl]benzene and (viii) 1,3-bis[4-(3-aminophenoxy)-3,5-dimethyl-α,α-dimethylbenzyl]benzene (hereafter for convenience, "1,4- or 1,3-" will be referred to as "1,4 (1,3)-").

Typically, it has been found that compounds (iii)–(viii) will provide even better flexibility and moldability/workability than the first two compounds (i) and (ii).

There are known techniques for reducing a bis(4-nitrophenoxy) compound obtained by reacting a bisphenol with 4-chloronitrobenzene in order to prepare a corresponding diamine. For example, bis(4-aminophenoxy)biphenyl has been manufactured by reducing bis(4-nitrophenoxy)biphenyl obtained from 4,4'-biphenol and 4-chloronitrobenzene [28th National Sampe Symposium, Apr. 12–14, p. 728–736 (1983)]. Furthermore, 2,2'-bis(4-aminophenoxy)propane has been manufactured from 2,2'-bis(4-hydroxyphenyl)propane [Roxz Chem., 48, p. 1459 (1974)]. However, a diamine compound having a structure of formula (I) according to the present invention has not been so produced.

In order to obtain a diamine compound of formula (I), it is necessary to pass through two steps of condensation and reduction. For example, when producing 1,4 (1,3)-bis[4-(4-aminophenoxy)-α,α-dimethylbenzyl]benzene, 1,4 (1,3)-bis(4-hydroxy-α,α-dimethylbenzyl]benzene), which has a structure represented by formula (II), is reacted with 4-chloronitrobanzene in the presence of a base in an aprotic polar solvent in order to prepare 1,4 (1,3)-bis[4-(4-nitrophenoxy)-α,α-dimethylbenzyl]benzene, which has a structure of formula (III).

The amount of 4-chloronitrobenzene is preferably two to three, more preferably 2.05 to 2.5 times more per mole of 1,4 (1,3)-bis(4-hydroxy-α,α-dimethylbenzyl]benzene.

Examples of suitable bases include carbonates, hydrogencarbonates, hydroxides and alkoxides of alkaline metals. Typical examples of these bases include potassium carbonate, sodium carbonate, potassium hydrogencarbonate, sodium hydrogencarbonate, potassium hydroxide, sodium hydroxide, lithium hydroxide, sodium methoxide and potassium isopropoxide. Among these, potassium carbonate, sodium hydroxide and potassium hydroxide are most preferably used and are also preferred from an economical viewpoint. The amount of the base is preferably not less than 2 equivalents, more preferably 2.2 to 3 equivalents when 1,4 (1,3)-bis(4-hydroxy-α,α-dimethylbenzyl)benzene is the raw material.

As the solvent used in the above described condensation reaction, aprotic polar solvents are suitable. Typical examples of these solvents include dimethyl sulfoxide, N,N-dimethylformamide, N,N'-dimethylacetamide, N-methylpyrrolidone, 1,3-dimethyl-2-imidazolidinone, hexamethylphosphortriamide and sulfolane. The amount of the solvent is preferably 1 to 1 to 15 times, more preferably 2 to 5 times the total weight of raw materials.

The reaction temperature may range from 50° to 220° C., and is preferably in the range of 80° to 180° C.

The end point of the reaction can be determined by observing a decrease of raw materials and unreacted intermediate through thin-layer chromatography or high-speed liquid chromatography.

This exemplified condensation reaction may be carried out by placing predetermined amounts of 1,4 (1,3)-bis(4-hydroxy-α,α-dimethylbenzyl)benzene, the base and the solvent in a reactor and forming an alkaline metal salt of 1,4(1,3)-bis(4-hydroxy-α,α-dimethylbenzyl)benzene. Then, 4-chloronitrobenzene can be added thereto. Alternatively, all the raw materials, including 4-chloronitrobenzene can be initially placed in the reactor. However, the reaction is not limited to these procedures, and can be carried out using other suitable procedures.

After completion of the reaction to obtain the intermediate represented by the formula (III), (e.g., 1,4 (1,3)-bis(4-(4-nitrophenoxy)-α,α-dimethylbenzyl)benzene), optional steps can be performed. For example, the concentration of the solvent can be modified or the reaction solution can be discharged into water.

The intermediate of formula (III) is then reduced to prepare the desired compound represented by the formula (I) (e.g., 1,4(1,3)-bis[4-(4-aminophenoxy)-α,α-dimethylbenzyl]benzene). The reduction can be achieved by standard procedures such as those which involve reducing a nitro group to an amino group. But, in an industrial context catalytic reduction or hydrazine reduction is preferred.

In the case of catalytic reduction, the reduction reaction is carried out using a reduction catalyst such as a metallic catalyst or a carrier catalyst of nickel, palladium or platinum or a Raney catalyst of nickel or copper in an amount of 0.01 to 10% (by weight) in terms of the metal with respect to the intermediate, e.g., 1,4(1,3)-bis[4-(4-nitrophenoxy)-α,α-dimethylbenzyl]benzene.

In the reduction reaction a solvent is used. Preferable examples of the solvent include methanol, ethanol, isopropyl alcohol, methyl cellosolve and N,N-dimethylformamide which are inactive in the reaction. There is no particular limitation on the reaction temperature, but it may be in the range of from 20° to 200° C., preferably 20° to 100° C. The reaction pressure maybe from atmospheric to about 50 atm.

In the case of hydrazine reduction, the reduction reaction is carried out using hydrazine in amount which exceeds the theoretical amount by 1.1 to 5 times.

The catalyst can be those metallic catalyst usually employed with catalytic reduction. The particularly preferable datalyst, however, is palladium/carbon, platinum/carbon or that which is prepared by allowing active carbon to adsorb ferric chloride. The amount of the catalyst may range from 0.001 to 30% (by weight) in terms of a metal with respect to the intermediate, e.g., 1,4(1,3)-bis[4-(4-nitrophenoxy)-α,α-dimethylbenzyl]-benzene.

As a reaction solvent which can be used in this process, those same solvents can be used which are useful with catalytic reduction. There is no particular restriction on reaction temperature. But it may usually be in the range of from 20° to 150° C., preferably 40° to 120° C.

After completion of the reaction, the reaction solution is hot-filtrated and can be subjected to optional treatments such as cooling, concentration, dilution and crystallization in order to obtain desired crystals of the product (e.g., 1,4 (1,3)-bis[4-aminophenoxy)-α,α-dimethylbenzyl]benzene). The crystals can be purified by suitable techniques such as washing and recrystallization.

The novel diamine according to the invention (e.g., 1,4 (1,3)-bis[4-(4-aminophenoxy)-α,α-dimethylbenzyl]benzene can be used to prepare polyimide resins, polyamide resins, bismaleimide resins or an epoxy resin using known techniques.

It will be appreciated that 1,4 (1,3)-bis,[4-(4-aminophenoxy)-3,5-dimethyl-α,α-dimethylbenzyl]benzene, which is one of the diamine compounds of the present invention, can be prepared by the above-mentioned procedure except that 1,4 (1,3)-bis(4-hydroxy-3,5-dimethyl-α,α-dimethylbenzyl)benzene is used as the compound of the formula (II). Furthermore, 1,4(1,3)-bis[4-(3-aminophenoxy)-α,α-dimethylbenzyl]benzene can be prepared by the above-mentioned procedure except that 4-chloronitrobenzene is replaced with m-dinitrobenzene. In other words, various diamine compounds of the present invention can be obtained by varying the combination of the compound of formula (II) and the nitrobenzene compound.

The bismaleimide compound of the present invention can be prepared using a dehydration/condensation reaction between a diamine component represented by formula (I) and maleic anhydride. As a result of this reaction, amino groups present at the opposite ends of formula (I) are replaced with maleimide groups.

The dehydration/condensation reaction involves dissolving or dispersing the diamine, maleic anhydride and an acid catalyst in a predetermined solvent. Then, the resulting solution is heated under reflux.

Preferable examples of the acid catalyst include mineral acids such as sulfuric acid, hydrochloric acid and phosphoric acid; heteropolyacids such as phosphotungstic acid and phosphomolybdic acid; organic sulfonic acids such as p-toluenesulfonic acid and methanesulfonic acid; halogenated carboxylic acids such as trichloroacetic acid and trifluoroacetic acid; solid acids such as silica-alumina; and cation exchange type ion exchange resins. In particular, sulfuric acid, phosphoric acid and p-tolunenesulfonic acid are preferred. In addition, the acids may be in the form of salts with diamines.

The amount of acid catalyst depends upon its type. But it may usually be in the range of from 0.1 to 10% by weight with respect to the total weight of maleic anhydride and the diamine. When the amount of the catalyst is less than 0.1% by weight, the expected effect of the catalyst will not always be achieved. When the amount is more than 10% by weight, no additional effect should be obtained from the catalyst, which is uneconomical. In addition, it is inconvenient and difficult to remove the excess catalyst.

Examples of suitable solvents to be used in the condensation reaction include aliphatic and alicyclic hydrocarbons such as hexane, heptane, decane and cyclohexane; aromatic hydrocarbons such as benzene, toluene and xylene; halides of these aliphatic and aromatic hydrocarbons; oxygen-containing, nitrogen-containing and sulfur-containing polar solvents such as dimethylformamide, N-methylpyrrolidone, acetonitrile, dimethylacetamide, dimethyl sulfoxide, sulfolane, anisole and n-butyl ether; and mixtures thereof. The amount of the solvent is preferably 1 to 20 times, particularly preferably 3 to 10 times as much as the total weight of the diamine component and maleic anhydride.

The reaction temperature under heating and reflux depends slightly upon the type of solvent. However, it may usually be in the range of from 80° to 190° C., preferably from 100° to 160° C. High pressure, atmospheric pressure or a reduced pressure can all be used, and will typically be selected to be compatible with the type of solvent and reaction temperature.

The reaction time may usually be in the range of from 2 to 10 hours, preferably 5 to 6 hours.

With regard to the amounts of maleic anhydride and diamine component, it is desirable that the amount of maleic anhydride is slightly in excess relative to that of the diamine component. In general, the molar ratio of maleic anhydride to diamine is preferably 2.05 to 3.0.

After completion of the condensation reaction, the reaction mixture is washed with water to remove any remaining catalyst and unreacted maleic anhydride therefrom. The solvent is then distilled off, thereby obtaining a concentrate. Afterward, alcohol is added to the concentrate, followed by stirring, so that a crystal powder is obtained. The resulting crude crystals can then be purified by recrystallization.

In order to obtain the thermosetting resin forming composition, and ultimately the resin, of the present invention from the bismaleimide compound and the diamine compound, it is preferred that a bismaleimide compound represented by formula (IV) be mixed with an aromatic diamine compound represented by formula (I) in the absence of any solvent or in the presence of an organic solvent. The mixture can then be subjected to heat treatment at a temperature of from 70° to 220° C. to carry out prepolymerization; the mixture and the prepolymer both being "resin forming compositions". Thereafter, the resin can be produced.

The following procedures are preferably employed. (1) The bismaleimide compound and the aromatic diamine compound can be mixed and then ground to a solid-solid state, wherein the ground mixture is used. Alternatively, the mixture can be further subjected to heat treatment to form a prepolymer. The prepolymer can then be ground to pellets or powder. In this case, heating conditions wherein the material is partially cured to the level of the prepolymer are preferable. In general, it is appropriate that the heat treatment is effected at a temperature of from 70° to 220° C. for 5 to 240 minutes, preferably at 80° to 200° C. for 10 to 180 minutes.

Or, (2) The bismaleimide compound and the aromatic diamine compound can be dissolved in an organic solvent. Then, the solution can be discharged into a poor solvent. The resulting precipitate can be collected by filtration, dried and then formed into pellets or powder. Alternatively, the bismaleimide compound and the aromatic diamine compound can be dissolved in an organic solvent, and then partially cured up to the level of a prepolymer by heat treatment. Afterward, the cured material can be discharged into a poor solvent. The resulting precipitate can be collected by filtration, dried and then formed into pellets or powder. Conditions for the heat treatment depend slightly upon the type of organic solvent, but they are generally consistent with those used for heat treatment according to procedure (1).

The organic solvent should not substantially react with both components, but should be a good solvent for both components. Examples of suitable solvents include halogenated hydrocarbons such as methylene chloride, dichloroethane and trichloroethylene; ketones such as acetone, methyl ethyl ketone, cyclo-hexanone and di-isopropyl ketone; ethers such as tetra-hydrofuran, dioxane and methyl cellosolve; aromatic compounds such as benzene, toluene and chlorobenzene; and aprotic polar solvents such as acetonitrile, N,N-dimethylformamide, N,N-dimethylacetamide, dimethyl sulfoxide, N-methyl-2-pyrrolidone and 1,3-dimethyl-2-imidazolidinone.

The ratio between the bismaleimide compound and the diamine compound is from 0.1 to 1.2 moles, preferably 0.2 to 0.8 mole of diamine compound per mole of the bismaleimide compound. When the ratio is too small, the resulting cured product will not have good impact resistance or flexibility. When it is too large, the cured product is adversely affected in terms of heat resistance.

Additional components can be added to the thermosetting resin forming composition of the present invention, so long as the objects of the present invention are not impaired. For example, a curing accelerator can be added. Suitable accelerators include radical polymerization initiators such as azo compounds or organic peroxides, or ionic catalysts such as tertiary amines, quaternary ammonium salts, imidazoles or boron trifluoride-amine salts.

Powdery reinforcing material and fillers can also be used. Examples include metal oxides such as aluminum oxide or magnesium oxide; metal hydroxides such as aluminum hydroxide; metal carbonates such as calcium carbonate or magnesium carbonate; diatomaceous earth powders; basic magnesium silicates; calcined clays; finely powdered silica; melted silica; crystalline silica, carbon black; kaolin; finely powdered mica; quartz powder; graphite; asbestos; molybdenum disulfide; or antimony trioxide.

Also, fibrous reinforcing materials and fillers can be added. Examples include inorganic fibers such as glass fiber, rock wool, ceramic fiber alumina fiber, potassium titanate fiber or carbon fiber; or organic fibers such as an aromatic polyamide.

For improving properties of the resin in a final product such as a coating film, adhesive layer or molded article, a synthetic resin can be added and blended therewith. This type of synthetic resin is, for example, a thermosetting resin such as a phenol resin, an epoxy resin, a melamine resin or a silicone resin; polyamide; polycarbonate; polysulfone; polyether sulfone; polyether ether ketone; modified polyphenylene oxide; polyphenylene sulfide; polyether imide; or a fluorine-containing resin.

The thermosetting resin according to the present invention can be molded by known molding methods such as compression molding, transfer molding, extrusion molding or injection molding, and then effectively put to practical use.

The present invention will be described in further detail by reference to the following examples. However, these examples should not be construed as in any way limiting the invention.

EXAMPLE 1A

In a reactor equipped with a stirrer, a reflux condenser, a thermometer, a Dean/Stark water separator and a nitrogen inlet pipe, there were placed 1410 g of N,N-dimethylformamide from which water had been removed, 207.6 g (0.6 mole) of 1,4-bis(4-hydroxy-α,α-dimethylbenzyl)benzene, 193.7 g (1.23 mole) of 4-chloronitrobenzene and 248.8 g (1.8 moles) of potassium carbonate, and 50 g of toluene was then added thereto.

The resulting mixture was heated, and stirring was continued for 5 hours, while a temperature of from 140° to 150° C. was maintained, in order to carry out the reaction. Water produced by the reaction was successively removed from the system by azeotropy with toluene.

After completion of the reaction, the resulting inorganic salts were removed by hot filtration. The filtrate was then heated again. While a temperature of from 90° to 95° C. was maintained, 210 g of water was added thereto over 2 hours in order to precipitate 1,4-bis[4-(4-nitrophenoxy)-α,α-dimethylbenzyl]benzene. This solution containing the precipitate was slowly cooled, and the resulting light yellow crystals were collected by filtration and then washed with a mixed solvent of N,N-dimethylformamide and methanol. Afterward, the resulting sludge was washed with 1 liter of methanol, filtered and then dried, thereby obtaining 335 g of light yellow powder.

Using high-speed liquid chromatography, the purity of the product was determined as being 99.3%. The analytical results were as follows:

Melting point: 186.5° to 188.5° C. Values of elemental analysis:

|  | C | H | N |
|---|---|---|---|
| Calcd. (%) | 73.47 | 5.44 | 4.76 |
| Found (%) | 73.28 | 5.56 | 4.96 |

IR (KBr tablet method) 1330, 1500 cm$^{-1}$ (a nitro group) 1240 cm$^{-1}$ (an ether bond)

In a hermetic reduction reactor equipped with a stirrer and a thermometer there were placed 294 g (0.5 mole) of 1,4-bis[4-(4-nitrophenoxy)-α,α-dimethylbenzyl]benzene obtained from the preceding step, 1175 g of dimethylformamide and 17.5 g of a 5% Pd/C catalyst. A hydrogen gas was then introduced thereinto, while the solution was stirred vigorously.

Reaction was continued at a reaction temperature of from 30° to 40° C. for 4 hours. At this point, 67.2 liters of hydrogen had been absorbed by the solution. Since further absorption was not observed, the reaction was brought to an end.

After completion of the reaction, filtration was effected at room temperature to remove the Pd/C catalyst from the solution.

The resulting reaction solution was heated to 80° to 90° C. While this temperature was maintained, 500 g of water was added dropwise thereto over 2.5 hours in order to precipitate 1,4-bis[4-(4-aminophenoxy)-α,α-dimethylbenzyl]benzene. This reaction solution was slowly cooled, and the resulting white crystals were collected by filtration and then washed with a mixed solution of N,N-dimethylformamide and methanol and afterward with methanol, and dried, thereby obtaining 242.8 g of 1,4 bis[4-(4-aminophenoxy)-α,α-dimethylbenzyl]benzene.

Using high-speed liquid chromatography, the purity of the product was determined as being 99.2% (total yield 88.3%). The analytical results were as follows:

Melting point: 189° to 190.5° C. Values of elemental analysis:

|  | C | H | N |
|---|---|---|---|
| Calcd. (%) | 81.82 | 6.82 | 5.30 |
| Found (%) | 81.90 | 6.75 | 5.21 |

IR (KBr tablet method) 1620, 3320–3430 cm$^{-1}$ (an amino group) 1230 cm$^{-1}$ (an ether bond)

EXAMPLE 1B

In a reactor equipped with a stirrer, a reflux condenser, a thermometer, a Dean/Stark water separator and a nitrogen inlet pipe, there were placed 600 g of N,N-dimethylformamide from which water had been removed, 207.6 g (0.6 mole) of 1,3-bis(4-hydroxy-α,α-dimethylbenzyl)benzene, 193.7 g (1.23 mole) of 4-chloronitrobenzene and 248.8 g (1.8 moles) of potassium carbonate, and 50 g of toluene was then added thereto.

The resulting mixture was heated, and stirring was then continued for 5 hours, while a temperature of from 140° to 150° C. was maintained, in order to carry out the reaction. Water produced by the reaction was successively removed from the system by azeotropy with toluene.

After completion of the reaction, the resulting inorganic salts were removed by hot filtration. The filtrate was then heated again. While a temperature of from 90° to 95° C. was maintained, 260 g of water was added thereto over 2 hours in order to precipitate 1,3-bis[4-(4-nitrophenoxy)-α,α-dimethylbenzyl]benzene. This solution containing the precipitate was slowly cooled, and the resulting light yellow crystals were collected by filtration and then washed with a mixed solvent of N,N-dimethylformamide and methanol. Afterward, the resulting sludge was washed with 1 liter of methanol, filtered and then dried, thereby obtaining 328 g of light yellow powder.

Using high-speed liquid chromatography, the purity of the product was determined as being 99.1%. The analytical results were as follows:

Melting point: 154.5° to 156.0° C. Values of elemental analysis:

|  | C | H | N |
|---|---|---|---|
| Calcd. (%) | 73.47 | 5.44 | 4.76 |
| Found (%) | 73.34 | 5.20 | 4.79 |

IR (KBr tablet method) 1330, 1490 cm$^{-1}$ (a nitro group) 1230 cm$^{-1}$ (an ether bond)

In a reactor equipped with a stirrer, a thermometer, a reflux condenser and a dropping funnel, there were placed 294 g (0.5 mole) of 1,3-bis[4-(4-nitrophenoxy)-α,α-dimethylbenzyl]benzene obtained from the preceding step. This material was then mixed with 1500 g of methyl cellosolve, 29.4 g of active carbon and 2.9 g of ferric chloride-hexahydrate. Afterward, stirring was continued for 3 hours, while a temperature of from 100° to 105° C. was maintained.

While the temperature was maintained, 150.2 g of 80% hydrazine monohydrate was added dropwise over 3 hours. Furthermore, the solution was aged at this temperature for 1 hour. Solids were then removed by hot filtration. Afterward, the resulting filtrate was concentrated and then recrystallized with isopropyl alcohol. White crystals of 1,3-bis[4-(4-amino-phenoxy)-α,α-dimethylbenzyl]benzene were obtained which was the desired compound.

The white crystals were then filtered, washed with isopropyl alcohol, and dried to obtain 228.5 g of 1,3-bis[4-(4-aminophenoxy)-α,α-dimethylbenzyl)benzene.

Using high-speed liquid chromatography, the purity of the product was determined as being 99.0% (total yield 81.4%). The analytical results were as follows:

Melting point: 103° to 105.5° C. Values of elemental analysis:

|  | C | H | N |
|---|---|---|---|
| Calcd. (%) | 81.82 | 6.82 | 5.30 |

-continued

|  | C | H | N |
|---|---|---|---|
| Found (%) | 81.86 | 6.45 | 5.22 |

IR (KBr tablet method) 1620, 3340–3440 cm$^{-1}$ (an amino group) 1240 cm$^{-1}$ (an ether bond)

EXAMPLE 1C

In a reactor equipped with a stirrer, a reflux condenser, a thermometer, a Dean/Stark water separator and a nitrogen inlet pipe, there were placed 400 g of N,N-dimethylformamide from which water had been removed, 161.0 g (0.4 mole) of 1,4-bis(4-hydroxy-3,5-dimethyl-α,α-dimethylbenzyl)benzene, 138.7 g (0.88 mole) of 4-chloronitrobenzene and 66.3 g (0.48 mole) of potassium carbonate, and 50 g of toluene was then added thereto.

The resulting mixture was heated, and stirring was then continued for 5 hours, while a temperature of from 140° to 150° C. was maintained, in order to carry out the reaction. Water produced by the reaction was successively removed from the system by azeotropy with toluene.

After completion of the reaction, the resulting inorganic salts were removed by hot filtration. The filtrate was cooled in to precipitate 1,4-bis[4-(4-nitrophenoxy)-3,5-dimethyl-α,α-dimethylbenzyl]benzene.

The precipitated light yellow crystals were collected by filtration, washed with 500 ml of methanol, and then dried. 245 g of light yellow powder was obtained.

Using high-speed liquid chromatography, the purity of the product was determined as 99.5%. The analytical results were as follows:

Melting point: 224° to 226° C. Values of elemental analysis:

|  | C | H | N |
|---|---|---|---|
| Calcd. (%) | 74.51 | 6.25 | 4.34 |
| Found (%) | 73.94 | 5.92 | 4.54 |

IR (KBr tablet method) 1345, 1515 cm$^{-1}$ (a nitro group) 1250 cm$^{-1}$ (an ether bond)

In a hermetic reduction reactor equipped with a stirrer and a thermometer there were placed 129.0 g (0.2 mole) of 1,4-bis[4-(4-nitrophenoxy)-3,5-dimethyl-α,α-dimethylbenzyl]benzene obtained from the preceding step, 322 g of N,N-dimethylformamide and 2.6 g of a 5% Pd/C catalyst. A hydrogen gas was then introduced thereinto, while the solution was stirred vigorously.

Reaction was continued at a reaction temperature of from 30° to 40° C. for 4 hours. At this point, 26.9 liters of hydrogen had been absorbed by the solution. Since further absorption was not observed the reaction was brought to an end.

After completion of the reaction, filtration was effected at room temperature to remove the Pd/C catalyst from the solution.

The resulting reaction solution was heated to 80° to 90° C. While this temperature was maintained, 80 g of water was added dropwise thereby over 2 hours in order to precipitate 1,4-bis[4-(4-aminophenoxy)-3,5-dimethyl-α,α-dimethylbenzyl]benzene. The reaction solution was slowly cooled, and the resulting light yellow crystals were collected by filtration, washed with 200 ml of methanol, and then dried, thereby obtaining 104.7 g of 1,4-bis[4-(4-aminophenoxy)-3,5-dimethyl-α,α-dimethylbenzyl]benzene.

Using high-speed liquid chromatography, the purity of the product was determined as being 99.2 % (total yield 85.0%). The analytical results were as follows:

Melting point: 228° to 230° C. Values of elemental analysis:

|  | C | H | N |
|---|---|---|---|
| Calcd. (%) | 82.15 | 7.58 | 4.79 |
| Found (%) | 82.09 | 7.13 | 4.84 |

IR (KBr tablet method) 1630, 3320–3430 cm$^{-1}$ (an amino group) 1240 cm$^{-1}$ (an ether bond)

EXAMPLE 1D

In a reactor equipped with a stirrer, a reflux condenser, a thermometer, a Dean/stark water separator and a nitrogen inlet pipe, there were placed 400 g Of N,N-dimethylformamide from which water had been removed, 138.4 g (0.4 mole) of 1,4-bis(4-hydroxy-α,α-dimethylbenzyl)benzene, 147.8 g (0.88 mole) of m-dinitrobenzene and 66.3 g (0.48 mole) of potassium carbonate, and 50 g of toluene was then added thereto.

The resulting mixture was heated, and stirring was then continued for 5 hours, while a temperature of from 140° to 150° C. was maintained, in order to carry out the reaction. Water produced by the reaction was successively removed from the system by azeotropy with toluene.

After completion of the reaction, the resulting inorganic salts were removed by hot filtration. Then, the filtrate was heated again. While a temperature of from 90° to 95° C. was maintained, 112 g of water was added thereto over 2 hours in order to precipitate 1,4-bis[4-(3-nitrophenoxy)-α,α-dimethylbenzyl]benzene. This solution was slowly cooled, and the resulting faintly brown crystals were collected by filtration, washed with 500 ml of methanol, and then dried. 220 g of faintly brown powder was obtained.

Using high-speed liquid chromatography, the purity of the product was determined as being 99.3%. The analytical results were as follows:

Melting point: 123° to 125° C. Values of elemental analysis:

|  | C | H | N |
|---|---|---|---|
| Calcd. (%) | 73.45 | 5.48 | 4.76 |
| Found (%) | 73.53 | 5.39 | 4.74 |

IR (KBr tablet method) 1355, 1525 cm$^{-1}$ (a nitro group) 1240 cm$^{-1}$ (an ether bond)

In a hermetic reduction reactor equipped with a stirrer and a thermometer, there were placed 118 g (0.2 mole) of 1,4-bis[4-(3-nitrophenoxy)-α,α-dimethylbenzyl]benzene obtained from the preceding step, 295 g of N,N-dimethylformamide and 2.4 g of a 5% Pd/C catalyst. A hydrogen gas was then introduced thereinto, while the solution was stirred vigorously.

Reaction was continued at a reaction temperature of from 30° to 40° C. for 4 hours. At this point, 26.9 liters of hydrogen had been absorbed by the solution. Since further absorption was not observed, the reaction was brought to an end.

After completion of the reaction, filtration was effected at room temperature to remove the Pd/C catalyst from the solution.

The resulting reaction solution was heated to 80° to 90° C. While this temperature was maintained, 126 g of water was added dropwise thereto over 2 hours in order to precipitate 1,4-bis[4-(3-aminophenoxy)-α,α-dimethylbenzyl]benzene. The reaction solution was slowly cooled, and the resulting light yellow crystals were collected by filtration, washed with 200 ml of methanol, and then dried, thereby obtaining 90.3 g of 1,4-bis[4-(3-aminophenoxy)-α,α-dimethylbenzyl]benzene.

Using high-speed liquid chromatography, the purity of the product was determined as being 99.2% (total yield 80.0%). The analytical results were as follows:

Melting point: 138° to 140° C. Values of elemental analysis:

|  | C | H | N |
|---|---|---|---|
| Calcd. (%) | 81.79 | 6.86 | 5.30 |
| Found (%) | 81.43 | 6.79 | 5.27 |

IR (KBr tablet method) 1630, 3320–3430 cm$^{-1}$ (an amino group) 1240 cm$^{-1}$ (an ether bond)

EXAMPLE 1E

In a reactor equipped with a stirrer, a reflux condenser, a thermometer, a Dean/Stark water separator and a nitrogen inlet pipe, there were placed 400 g of N,N-dimethylformamide from which water had been removed, 138.6 g (0.4 mole) of 1,3-bis(4-hydroxy-α,α-dimethylbenzyl)benzene, 147.8 g (0.88 mole) of m-dinitrobenzene and 66.3 g (0.48 mole) of potassium carbonate, and 50 g of toluene was then added thereto.

The resulting mixture was heated, and stirring was then continued for 5 hours, while a temperature of from 140° to 150° C. was maintained, in order to carry out the reaction. Water produced by the reaction was successively removed from the system by azeotropy with toluene.

After completion of the reaction, the resulting inorganic salts were removed by filtration. Then, the filtrate was heated again. While a temperature of from 90° to 95° C. was maintained, 112 g of water was added thereto over 2 hours in order to precipitate 1,3-bis[4-(3-nitrophenoxy)-α,α-dimethylbenzyl]benzene. This solution was slowly cooled, and the resulting faintly brown crystals were collected by filtration, washed with 200 ml of methanol, and then dried. 215 g of faintly brown powder was obtained.

Using high-speed liquid chromatography, the purity of the product was determined as being 99.1%. The analytical results were as follows;

Melting point: 84° to 86° C. Values of elemental analysis:

|  | C | H | N |
|---|---|---|---|
| Calcd. (%) | 73.45 | 5.48 | 4.76 |
| Found (%) | 73.70 | 5.40 | 4.46 |

IR (KBr tablet method) 1330, 1510 cm$^{-1}$ (a nitro group) 1245 cm$^{-1}$ (an ether bond)

In a hermetic reduction reactor equipped with a stirrer and a thermometer, there were placed 118 g (0.2 mole) of 1,3-bis-[4-(3-nitrophenoxy)-α,α-dimethylbenzyl]benzene obtained from the preceding step, 295 g of N,N-dimethylformamide and 2.4 g of a 5% Pd/C catalyst. A hydrogen gas was then introduced thereinto, while the solution was stirred vigorously.

Reaction was continued at a reaction temperature of from 30° to 40° C. for 5 hours. At this point, 26.9 liters of hydrogen had been absorbed by the solution. Since further absorption was not observed any more, the reaction was brought to an end.

After completion of the reaction, filtration was effected at room temperature to remove the Pd/C catalyst from the solution.

The resulting reaction solution was heated to 80° to 90° C. While this temperature was maintained, 126 g of water was added dropwise thereto over 2 hours in order to precipitate 1,3-bis[4-(3-aminophenoxy)-α,α-dimethylbenzyl]benzene. The reaction solution was slowly cooled, and the resulting light yellow crystals were collected by filtration, recrystallized from methanol, and then dried, thereby obtaining 86.6 g of 1,3-bis[4-(3-aminophenoxy)-α,α-dimethylbenzyl)benzene.

Using high-speed liquid chromatography, the purity of the product was determined as being 99.0% (total yield 75.0%). The analytical results were as follows:

Melting point: 94° to 96° C. Values of elemental analysis:

|  | C | H | N |
|---|---|---|---|
| Calcd. (%) | 81.82 | 6.82 | 5.30 |
| Found (%) | 81.35 | 6.96 | 5.44 |

IR (KBr tablet method) 1625, 3340–3440 cm$^{-1}$ (an amino group) 1235 cm$^{-1}$ (an ether bond)

EXAMPLE 2A

In a reactor equipped with a stirrer, a thermometer, a reflux condenser having a water separator and a dropping funnel there were placed 26.5 g (0.27 mole) of maleic anhydride, 1.6 g of p-toluenesulfonic acid and 150 ml of toluene, and the temperature of the solution was increased to maintain the reflux condition of toluene. A solution prepared by dissolving 52.8 g (0.1 mole) of 1,3-bis[4-(4-aminophenoxy)-α,α-dimethylbenzyl]benzene formed in Example 1B in 100 ml of toluene was added dropwise to the above-mentioned solution through a dropping funnel over 7 hours. After completion of the addition, the solution was aged for 2 hours. Water produced by the reaction was collected by a water separator provided on the reflux condenser from the beginning of dropping to the end of aging. After completion of the reaction, the solution was cooled to 70° C., and 100 ml of warm water was added thereto. stirring followed at this temperature for 30 minutes. After standing, the lower layer (the water layer) of two separate layers was drawn out, and 100 ml of warm water was again added thereto. Washing and liquid separation followed in like manner.

The resulting upper layer of a toluene solution was finally concentrated in vacuum at a temperature of not more than 130° C. to obtain 68 g of reddish brown transparent resinous crude 1,3-bis[4-(4-maleimidophenoxy)-α,α-dimethylbenzyl]benzene which was the desired compound. Its yield was quantitative, and its purity according to HLC was 91%.

Afterward, the crude crystals were purified by recrystallization to obtain pure light yellow powder. The analytical results were as follows:

Melting point: 172° to 175° C. Values of elemental analysis ($C_{44}H_{36}N_2O_6$):

|  | C | H | N |
|---|---|---|---|
| Calcd. (%) | 76.70 | 5.27 | 4.07 |
| Found (%) | 76.20 | 5.43 | 4.22 |

Figure 1:
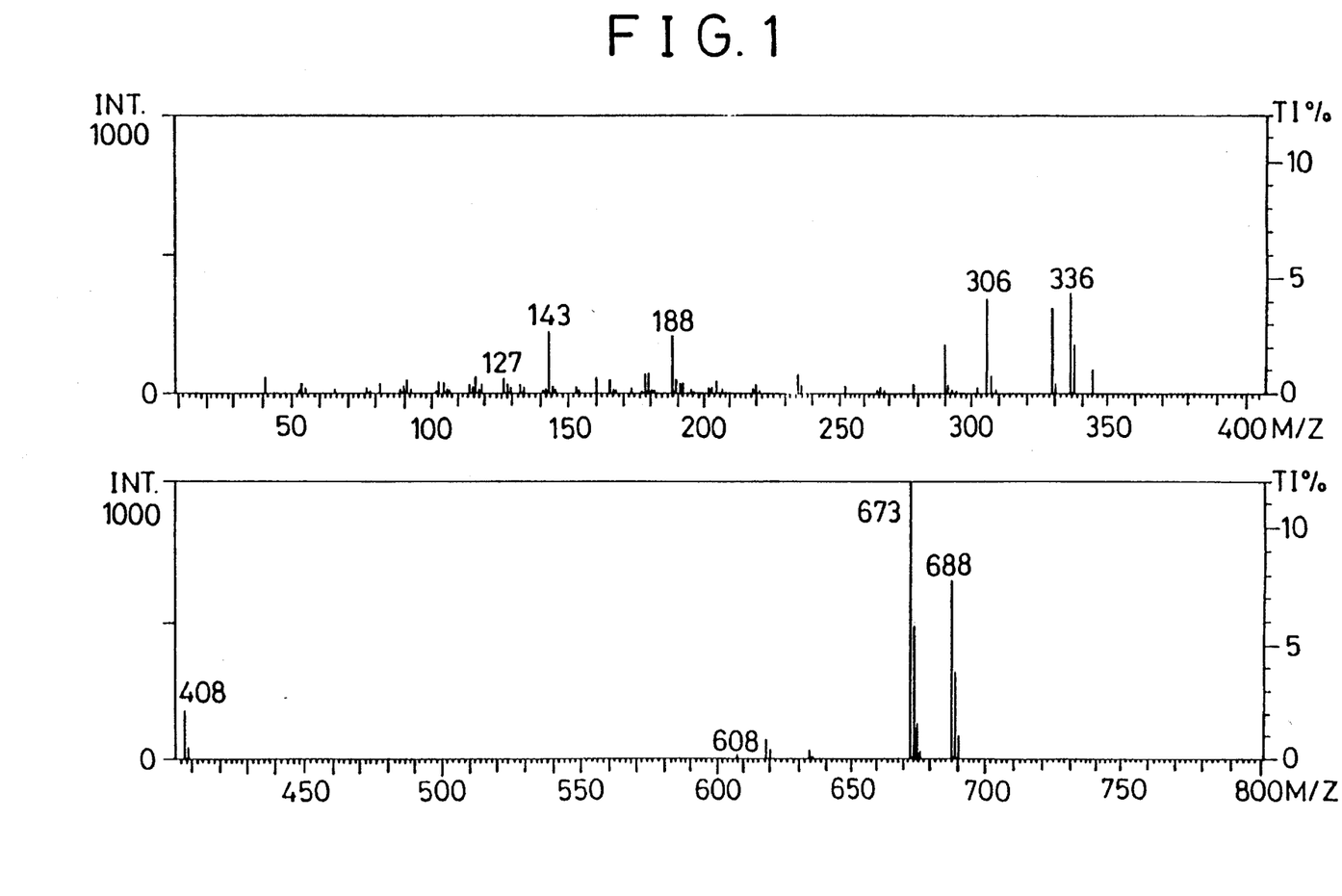
FIG. 1 is a mass spectrum of the bismaleimide compound of Example 2A.
Figure 2:
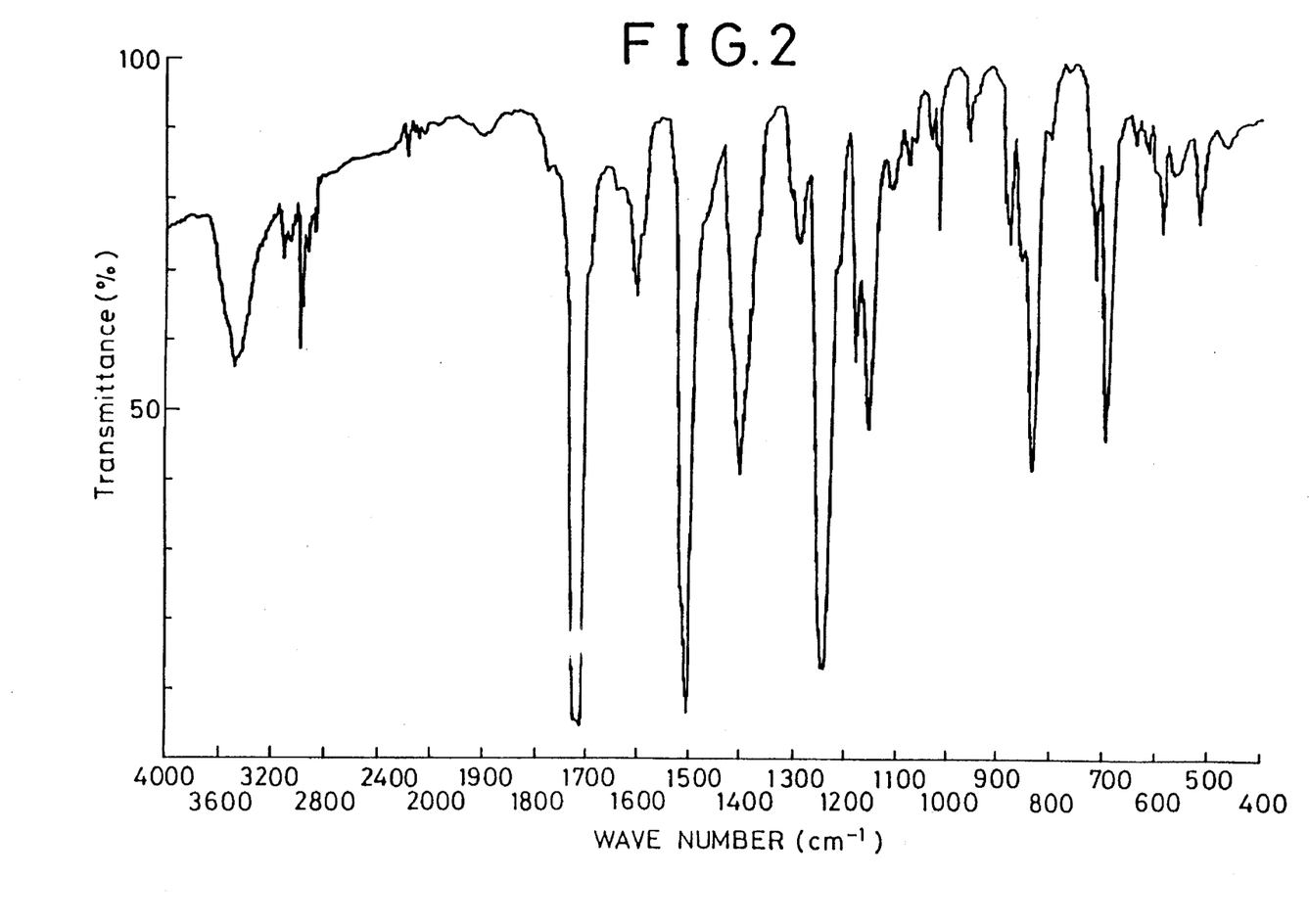
FIG. 2 is an IR spectrum of the bismaleimide compound of FIG. 1.

A mass spectrum is shown in FIG. 1, and an IR spectrum is shown in FIG. 2.

EXAMPLE 2B

In the same reactor used in Example 2A, there were placed 26.5 g (0.27 mole) of maleic anhydride, 0.7 g of phosphoric acid and 150 ml of mixed xylene. A solution was then added dropwise thereto under reflux of xylene, the solution having been prepared by thermally dissolving 52.8 g (0.1 mole) of 1,4-bis[4-(4-aminophenoxy),α,α-dimethylbenzyl)benzene obtained in Example 1A in a mixture of 100 ml of mixed xylene and 50 ml of N,N-dimethylformamide. A dropping time of 5 hours and an aging time of 2 hours were used in order to carry out the reaction. The reaction solution was concentrated to about ½ the original amount and then cooled. When a temperature of 80° C. had been reached; 50 g of water was added thereto. Afterward, the solution was slowly cooled with stirring, so that crystals were precipitated. The crystals were then cooled to room temperature, filtered, and washed with cold methanol. 66.5 g of desired crude 1,4-bis[4-(4-maleimidophenoxy)-α,α-dimethylbenzyl]benzene was obtained. Its yield was 96.7%, and its purity according to HLC was 97.5%.

The product was then purified by recrystallization from toluene in order to obtain pure light yellow powder. The analytical results were as follows:

Melting point: 214° to 216° C. Values of elemental analysis ($C_{44}H_{36}N_2O_6$):

|  | C | H | N |
|---|---|---|---|
| Calcd. (%) | 76.70 | 5.27 | 4.07 |
| Found (%) | 76.02 | 5.51 | 4.18 |

The results of a mass spectrum were the same as for the compound of Example 2A (M/Z; M+ 688, 673, 408).

Experiment 1

With regard to the bismaleimides obtained in Examples 2A and 2B, their solubility in some solvents were investigated. The results are set forth in Table 1.

TABLE 1

| Solvent | Solubility of Bismaleimide in Solvent* (g/100 ml) | | |
|---|---|---|---|
| | Compound of Example 2A | Compound of Example 2B | N,N'(Methylene-di-P-phenylene)-bismaleimide |
| Toluene | >50 | 8 | <1 |
| Tetrahydrofuran | >50 | 12 | 6 |
| Methylene Chloride | <50 | 15 | 8 |

*Measurement was made at 25° C.

EXAMPLE 2C

In a reactor equipped with a stirrer, a thermometer, a reflux condenser having a water separator and a dropping funnel there were placed 26.5 g (0.27 mole) of maleic anhydride, 1.6 g of p-toluenesulfonic acid and 150 ml of toluene. The temperature of the solution was increased to maintain the reflux condition of toluene. A solution prepared by dissolving 58.8 g (0.1 mole) of 1,4-bis[4-(4 -aminophenoxy)-3,5-dimethyl-α,α-dimethylbenzyl]benzene formed in Example 1C in 100 ml of toluene was added dropwise to the above-mentioned solution through a dropping funnel over 7 hours. After completion of the addition, the solution was aged for 2 hours. Water produced by the reaction was collected by a water separator provided on the reflux condenser from the beginning of dropping to the end of aging. After completion of the reaction, the solution was cooled to 70° C., and 100 ml of warm water was added thereto. Stirring followed at this temperature for 30 minutes. After standing, the lower layer (the water layer) of two separate layers was drawn out, and 100 ml of warm water was again added thereto. Washing and liquid separation followed in like manner.

The resulting upper layer of a toluene solution was cooled in order to precipitate light yellow crude 1,4-bis[4-(4-maleimidophenoxy)-3,5-dimethyl-α,α-dimethylbenzyl]benzene, which was collected by filtration and then dried. 65.2 g of product was obtained.

Its yield was 87.5%, and its purity according to HLC was 96.4%.

Afterward, the crude crystals were purified by recrystallization to obtain a pure light yellow powder. The analytical results were as follows:

Melting point: 232.5° to 235° C. Values of elemental analysis ($C_{48}H_{44}N_2O_6$):

| | C | H | N |
|---|---|---|---|
| Calcd. (%) | 77.38 | 5.95 | 3.76 |
| Found (%) | 77.05 | 6.08 | 3.66 |

Figure 3:
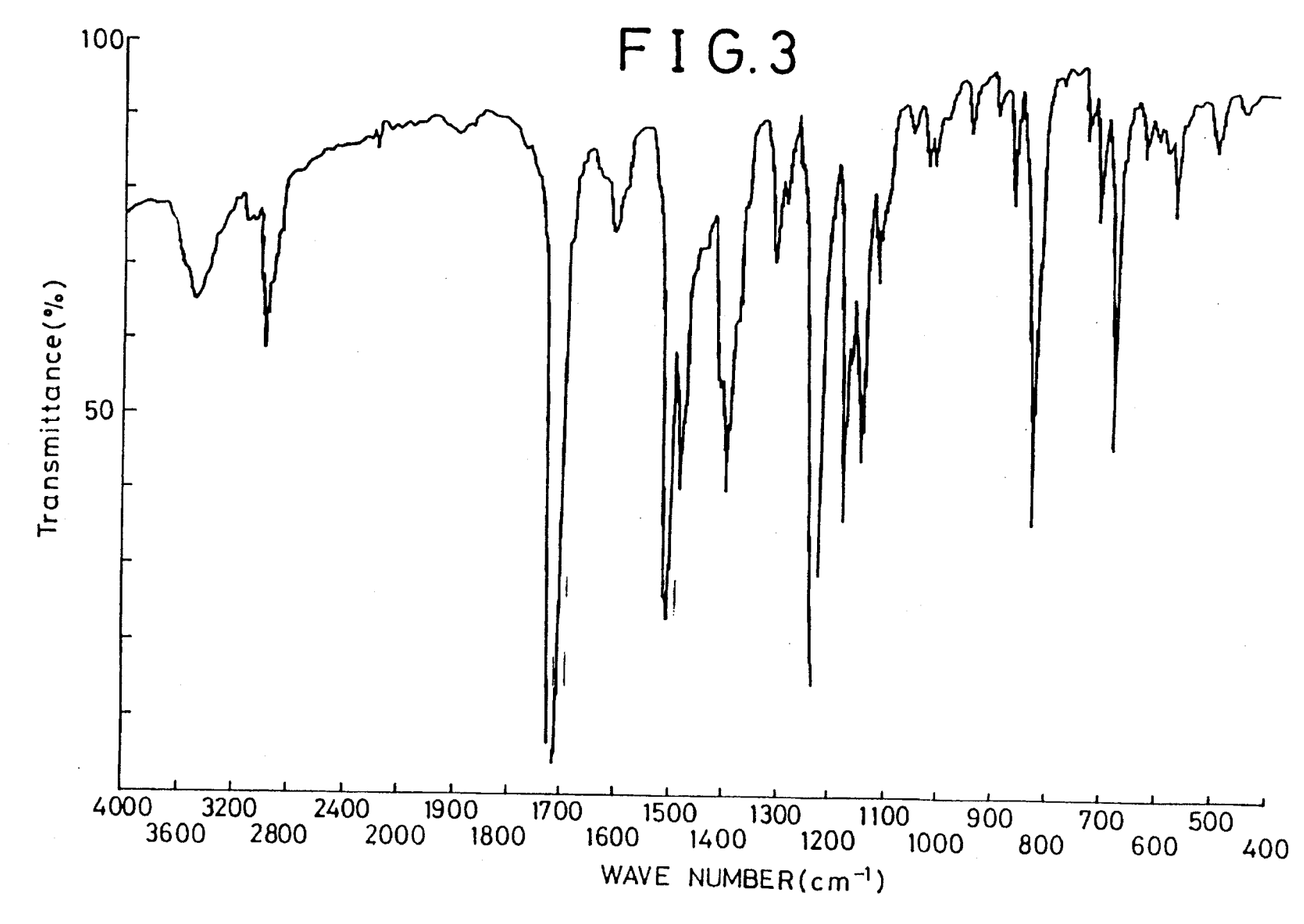
FIGS. 3 and 4 are IR spectra of the bismaleimide compounds of Examples 2C and 2D, respectively.

An IR spectrum of the product is shown in FIG. 3.

EXAMPLE 2D

In a reactor equipped with a stirrer, a thermometer, a reflux condenser having a water separator and a dropping funnel there were placed 26.5 g (0.27 mole) of maleic anhydride, 1.6 g of p-toluenesulfonic acid and 150 ml of toluene. The temperature of the solution was increased to maintain the reflux condition of toluene. A solution prepared by dissolving 52.8 g (0.1 mole) of 1,3 bis[4-(3-aminophenoxy)-α,α-dimethyl-benzyl]benzene formed in Example 1E in 100 ml of toluene was added dropwise to the above-mentioned solution through a dropping funnel over 7 hours. After completion of the addition, the solution was aged for 2 hours. Water produced by the reaction was collected by a water separator provided on the reflux condenser from the beginning of dropping to the end of aging. After completion of the reaction, the solution was cooled to 70° C., and 100 ml of warm water was added thereto. Stirring followed at this temperature for 30 minutes. After standing, the lower layer (the water layer) of two separate layers was drawn out, and 100 ml of warm water was again added thereto. Washing and liquid separation followed in like manner.

The resulting upper layer of a toluene solution was finally concentrated in vacuo at a temperature of not more than 130° C. to obtain 68.2 g of reddish brown transparent resinous crude 1,3-bis[4-(3-maleimidophenoxy)-α,α-dimethylbenzyl]benzene. This was the desired compound.

Its yield was quantitative, and its purity according to MLC was 96.3%.

Afterward, the crude crystals were purified by column chromatography to obtain a pure light yellow resinous product.

Elemental analysis ($C_{44}H_{36}N_2O_6$):

| | C | H | N |
|---|---|---|---|
| Calcd. (%) | 76.70 | 5.27 | 4.07 |
| Found (%) | 76.41 | 5.44 | 4.01 |

Mass spectrum M/Z; $M^+$ 688, 673, 408

Figure 4:
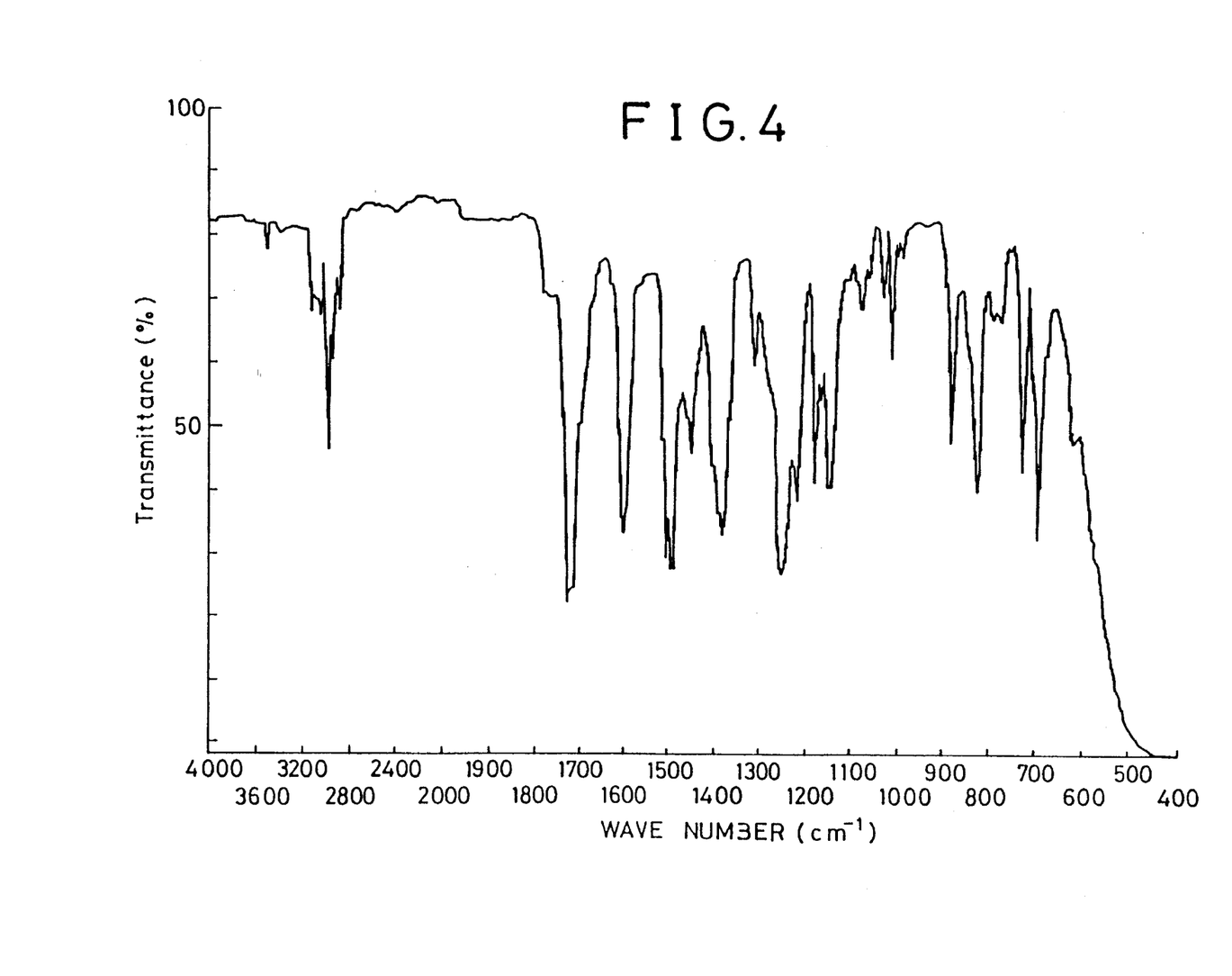

An IR spectrum of the product is shown in FIG. 4.

EXAMPLE 2E

In the same reactor used in Example 2D, there were placed 26.5 g (0.27 mole) of maleic anhydride, 0.7 g of phosphoric acid and 150 ml of mixed xylene. A solution was then added dropwise thereto, the solution having been prepared by thermally dissolving 52.8 g (0.1 mole) of 1,4-bis[4-(3-aminophenoxy)-α,α-dimethylbenzyl]benzene obtained in Example 1D in a mixture of 100 ml of mixed xylene and 50 ml of N,N-dimethylformamide. A dropping time of 5 hours and an aging time of 2 hours were used in order to carry out the reaction. The reaction solution was concentrated to about ½ the original amount and then cooled. When a temperature of 80° C. had been reached, 50 g of water was added thereto. Afterward, the solution was slowly cooled, so that crystals precipitated. The precipitated crystals were then cooled to room temperatures filtered; and washed with cold methanol. 67.1 g of desired crude 1,4-bis [4-(3-maleimidophenoxy)-α,α-dimethylbenzyl]benzene was obtained.

Its yield was 94.8%, and its purity according to HLC was 92.0%.

The product was then purified by recrystallization from toluene in order to obtain pure light yellow powder. The analytical results were as follows:

Melting point: 192° to 193° C. Elemental analysis ($C_{44}H_{36}N_2O_6$):

|  | C | H | N |
|---|---|---|---|
| Calcd. (%) | 76.70 | 5.27 | 4.07 |
| Found (%) | 76.66 | 5.33 | 4.18 |

The results of a mass spectrum were the same as from the compound from Example 2D (M/Z; M$^+$ 688, 673, 408).

EXAMPLEs 3A to 3C and Comparative Examples 3A and 3B

In a reactor equipped with a stirrer, a reflux condenser and a nitrogen inlet pipe, there were placed 1,3-bis[4-(4-maleimidophenoxy)-α,α-dimethylbenzyl]benzene obtained in Example 2A and 1,3-bis[4-(4-aminophenoxy)α,α-dimethylbenzyl]benzene obtained in Example 1B in the molar ratio set forth in Table 2. They were then heated and melted at 180° C. for 20 minutes. Then, they were defoamed at 150° C. under reduced pressure (from 10 to 15 mmHg) for 30 minutes. Afterward, the mixture was cooled to room temperature, thereby obtaining a brown transparent glassy solidified resin forming composition. A mold which had been heated to 180° C. was filled with the resin forming composition, while the resin composition was heated and melted. The composition was maintained at 200° C. under 50 kg/cm$^2$ for 30 minutes. After this compression molding, the molded material was taken out of the mold and postcured in an oven at 250° C. for 4 hours. Cured test pieces (length 127 mm, width 12.7 mm and thickness 6.4 mm) were obtained.

For these test pieces, bending strength, flexural modulus, the starting temperature of thermal decomposition and hygroscopicity were measured, and the results are set forth in Table 2.

COMPARATIVE EXAMPLE 3C

N,N'4,4'-Diphenylmethanebismaleimide and 4,4'diaminodiphenylmethane were used to prepare a composition (molar ratio 2/1) shown in Table 2. Afterward, the same operation explained with respect to Examples 3A to 3C was followed, and the results set forth in Table 2 were obtained.

COMPARATIVE EXAMPLE 3D

Kelimide 601 (made by Nippon Polyimide Co., Ltd.) was used as a resin forming composition. afterward, the same operation explained with respect to Examples 3A to 3C was followed, and the results set forth in Table 2 were obtained.

EXAMPLES 3D TO 3G

In a stainless steel reactor equipped with a stirrer, a reflux condenser and a nitrogen inlet pipe, there were placed each of the bismaleimide compounds prepared in Examples 2A, 2D, 2C and 2E and each of the diamine compounds prepared in Examples 1A, 1C and 1B in the molar ratios shown in Table 3. N-methyl-2-pyrrolidone was poured into the solution in such an amount that the concentration of a resin was 55% by weight, followed by heating at 150° C. for 50 minutes. The resulting varnishy solution was discharged into water to form a precipitate. The precipitate was then collected by filtration, washed with water, and then dried with hot air at 80° C. for 15 hours. The product was further dried at 110° C. for 20 minutes, and additionally at 130° C. for 30 minutes. It was then ground in a mortar and then passed through a sieve of 60 mesh, to obtain a polyaminobismaleimide type thermosetting resin forming composition. Afterward, the same operation described with respect to Examples 3A to 3C was followed, and the results set forth in Table 3 were obtained.

In these examples, physical properties of thermosetting resins and the like were measured in the following manner.

Bending strength and flexural modulus were measured in accordance with ASTM-D-790.

Starting temperature of thermal decompositions was determined as the temperature at which weight begins to decrease and was measured at a temperature rise rate of 10° C./minute in air in accordance with the TGA method.

Izod impact strength was measured in accordance with ASTM-D 256.

Hygroscopicity was measured in accordance with ASTM-D570-63.

TABLE 2

| | Resin Forming Composition | |
|---|---|---|
| | Bismaleimide Compound (IV) | Diamine Compound (I) |
| Example 3A | 1,3-bis[4-(4-maleimidophenoxy)-α,α-dimethylbenzyl]benzene | 1,3-bis[4(4-aminophenoxy)-α,α-dimethylbenzyl]benzene |
| Example 3B | 1,3-bis[4-(4-maleimidophenoxy)-α,α-dimethylbenzyl]benzene | 1,3-bis[4(4-aminophenoxy)-α,α-dimethylbenzyl]benzene |
| Example 3C | 1,3-bis[4-(4-maleimidophenoxy)-α,α-dimethylbenzyl]benzene | 1,3-bis[4(4-aminophenoxy)-α,α-dimethylbenzyl]benzene |
| Comp. Ex. 3A | 1,3-bis[4-(4-maleimidophenoxy)-α,α-dimethylbenzyl]benzene | 1,3-bis[4(4-aminophenoxy)-α,α-dimethylbenzyl]benzene |
| Comp. Ex. 3B | 1,3-bis[4-(4-maleimidophenoxy)-α,α-dimethylbenzyl]benzene | 1,3-bis[4(4-aminophenoxy)-α,α-dimethylbenzyl]benzene |
| Comp. Ex. 3C | N,N',4,4'-diphenylmethanebismaleimide | 4,4'-diaminodiphenylmethane |
| Comp. Ex. 3D | Kelimide 601 | |

| | Molar ratio I/IV | Izod impact strength (no notch) (kg · cm/cm) | Bending strength (kg/mm$_2$) | Flexural modulus (kg/mm$_2$) | Temp. at 0.5% weight decrease (°C.) | Hygroscopicity (%) |
|---|---|---|---|---|---|---|
| Example 3A | 0.3 | 37 | 15.0 | 318 | 360 | 0.26 |
| Example 3B | 0.5 | 41 | 16.1 | 316 | 357 | 0.29 |

TABLE 2-continued

| | | | | | | |
|---|---|---|---|---|---|---|
| Example 3C  | 1.0 | 38 | 15.4 | 317 | 362 | 0.30 |
| Comp. Ex. 3A | 1.5 | 37 | 15.8 | 305 | 315 | 0.27 |
| Comp. Ex. 3B | 0   | 2  | 5.2  | 460 | 412 | 0.90 |
| Comp. Ex. 3C | 0.5 | 11 | 9.2  | 372 | 359 | 0.89 |
| Comp. Ex. 3D |     | 9  | 8.1  | 342 | 366 | 0.90 |

TABLE 3

| | Resin Forming Composition | |
|---|---|---|
| | Bismaleimide Compound (IV) | Diamine Compound (I) |
| Example 3D | 1,3-bis[4-(4-maleimidophenoxy)-α,α-dimethylbenzyl]benzene | 1,4-bis[4-(4-aminophenoxy)-α,α-dimethylbenzyl]benzene |
| Example 3E | 1,3-bis[4-(3-maleimidophenoxy)-α,α-dimethylbenzyl]benzene | 1,4-bis[4-(4-aminophenoxy)-3,5-dimethyl-α,α-dimethyl-benzyl]benzene |
| Example 3F | 1,4-bis[4-(4-maleimidophenoxy)-3,5-dimethyl-α,α-dimethyl-benzyl]benzene | 1,3-bis[4-(4-aminophenoxy)-α,α-dimethylbenzyl]benzene |
| Example 3G | 1,4-bis[4-(3-maleimidophenoxy)-α,α-dimethylbenzyl]benzene | 1,3-bis[4(-4-aminophenoxy)-α,α-dimethylbenzyl]benzene |

| | Molar ratio I/IV | Izod impact strength (no notch) (kg·cm/cm) | Bending strength (kg/mm$_2$) | Flexural modulus (kg/mm$_2$) | Temp. at 0.5% weight decrease (°C.) | Hygro-scopicity (%) |
|---|---|---|---|---|---|---|
| Example 3D | 0.5 | 37 | 15.5 | 325 | 362 | 0.27 |
| Example 3E | 0.5 | 35 | 15.7 | 320 | 359 | 0.24 |
| Example 3F | 0.5 | 35 | 15.0 | 340 | 360 | 0.29 |
| Example 3G | 0.5 | 36 | 14.8 | 332 | 356 | 0.26 |

What is claimed is:

1. A bismaleimide compound having a structure represented by the formula below:

wherein the R groups may be the same or different and are selected from the group of H and CH$_3$.

2. A compound according to claim 1, wherein the maleimido groups of the maleimidophenoxy groups are bonded at meta positions.

3. A compound according to claim 1, wherein the maleimido groups of the maleimidophenoxy groups are bonded at para positions.

4. A compound according to claim 1 selected from the group consisting of 1,3-bis[4-(4-maleimidophenoxy)-α,α-dimethylbenzyl]benzene, 1,3-bis[4-(3-maleimidophenoxy)-α,α-dimethylbenzyl]benzene, 1,3-bis[4-(4-maleimidophenoxy)-3,5-dimethyl-α,α-dimethylbenzyl]benzene, and 1,3-bis[4-(3-maleimidophenoxy)-3,5-dimethyl-α,α-dimethylbenzyl]benzene.

* * * * *

UNITED STATES PATENT AND TRADEMARK OFFICE
CERTIFICATE OF CORRECTION

PATENT NO. : 5,484,948

DATED: : January 16, 1996

INVENTOR(S) : Keizaburo YAMAGUCHI et al

It is certified that error appears in the above-identified patent and that said Letters Patent is hereby corrected as shown below:

On the title page:

[75] Inventors:

-- Keizaburo Yamaguchi, Chiba; Tatsuhiro Urakami, Yokohama; Midori Yamazaki, Hiratsuka; Akihiro Yamaguchi, Kamakura; all of Japan. --

[30] Foreign Application Priority Data

-- July 6, 1990 [JP] Japan ...................2-177517 --

Signed and Sealed this

Twenty-second Day of October, 1996

*Attest:*

BRUCE LEHMAN

*Attesting Officer*     *Commissioner of Patents and Trademarks*